Figure 1:
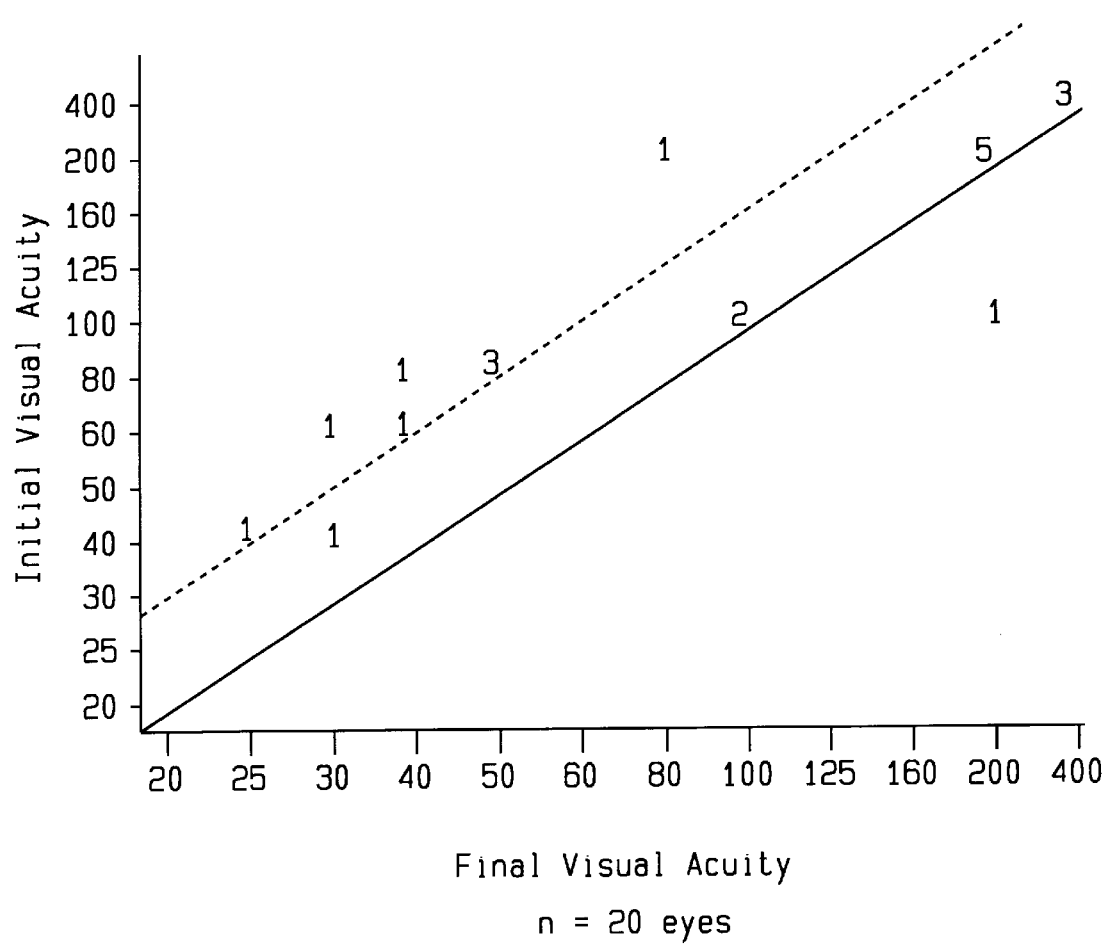

United States Patent [19]
Wirostko

[11] Patent Number: 6,015,803
[45] Date of Patent: Jan. 18, 2000

[54] ANTIBIOTIC TREATMENT OF AGE-RELATED MACULAR DEGENERATION

[76] Inventor: Emil Wirostko, 34 Old Mine Rd., Lebanon, N.J. 08833

[21] Appl. No.: 09/072,521

[22] Filed: May 5, 1998

[51] Int. Cl.$^7$ .................................................. A61K 31/00
[52] U.S. Cl. ............................................................ 514/152
[58] Field of Search ................................ 514/29, 30, 152

[56] References Cited

U.S. PATENT DOCUMENTS 5,207,660  5/1993  Lincoff .................................... 604/300

OTHER PUBLICATIONS

Bressler et al.: Age–related macular degeneration. *Surv. Opthalmol.* 32:375–413, 1988.
Penfold et al.: Senile macular degeneration: The involvement of giant cells in the atrophy of the retinal pigment epithelium. *Invest. Ophthalmol. Vis. Sci.* 27:364–371, 1986.
Penfold et al.: Age–related macular degeneration: Ultrastructural studies of the relationship of leucocytes to angiogenesis. *Graefe's Arch. Ophthalmol.* 2256:70–76, 1987.
Tilley et al.: Minocycline in rheumatoid arthritis. A forty–eight week double blind placebo controlled trial. MIRA trial Group. *Annals of Internal Medicine* 122(2):81–89, 1995.
Brown et al.: Diagnosis and treatment of ocular rosacea. *Ophthalmology* 85:779–786, 1978.
Salamon: Tetracyclines in ophthalmology. *Surv. Ophthalmol.* 29:265–275, 1985.
Bressler et al.: The grading and prevalence of macular degeneration in Chesapeake by Waterman. *Arch. Ophthalmol.* 107:847–852, 1989.
Smiddy et al.: Prognosis of patients with bilateral macular drusen. *Ophthalmology* 91:271–276, 1984.
Friedman et al.: Ocular blood flow velocity in age–related macular degeneration. *Ophthalmology* 102(4):640–646, 1995.
Hardy: Retina & Intraocular Tumors, in Vaughan et al. (ed): *General Ophthalmology* (4th ed), Appleton & Lange, Connecticut, 1995, pp. 186–188.
Fingeret et al.: Interferometry, in *Atlas of primary eyecare procedures,* Appleton & Lange, Connecticut, 1990, pp. 272–273.
Ratzenhofer et al., "In–vitro inhibition of collagenase activity in epidermolysis bullosa hereditaria dystrophica", *Z Hautkr,* Dec. 15, 1978, 53(24):929–34, [English abstract].
Miyachi et al., "Effect of antibiotics on the generation of reactive oxygen species", *J. Invest. Dermatol.,* Apr., 1986, 86(4):449–53.
Umeki, "Anti–inflammatory action of erythromycin: Its inhibitory effect on neutrophil NADPH oxidase activity", *Chest,* Oct., 1993, 104(4):1191–3.

*Primary Examiner*—Elli Peselev
*Attorney, Agent, or Firm*—Pennie & Edmonds LLP

[57] ABSTRACT

A method is provided for the treatment of age-related macular degeneration by administering various antibiotics, such as tetracycline and its derivatives, rifamycin and its derivatives, macrolides, and metronidazole, to a patient in a therapeutically effective amount.

6 Claims, 1 Drawing Sheet

ANTIBIOTIC TREATMENT OF AGE-RELATED MACULAR DEGENERATION

TABLE OF CONTENTS
1. BACKGROUND OF THE INVENTION
   1.1 TECHNICAL FIELD
   1.2 BACKGROUND OF ART
2. SUMMARY OF THE INVENTION
3. BRIEF DESCRIPTION OF THE DRAWINGS
4. DESCRIPTION OF PREFERRED EMBODIMENTS
5. CLAIMS
6. ABSTRACT OF THE DISCLOSURE
7. DRAWING
8. DECLARATION AND POWER OF ATTORNEY
9. DECLARATION OF SMALL ENTITY STATUS

1. BACKGROUND OF THE INVENTION

1.1 Tecnical Field

The present invention is directed to the treatment of age-related macular degeneration (ARMD) by the administration of certain antibiotics. In one embodiment, broad-spectrum bacteriostatic antibiotics, such as tetracycline-based antibiotics (TBA), are administered for up to fourteen (14) months, which leads to measurable improvements in some of the symptoms.

1.2 Background of Art

Age-related macular degeneration (ARMD) is the leading cause of blindness among persons over fifty in the United States and other countries (Bressler NM et al., Age-related macular degeneration. Sury. Ophthalmol. 1988; 32: 375–413). Two forms of age-related macular degeneration are known: (1) neovascular, also known as exudative, age-related macular degeneration (E-ARMD) and (2) nonneovascular, also known as nonexudative, age-related macular degeneration (NE-ARMD). NE-ARMD is characterized by the presence of drusen, yellow-white lesions of the retinal pigment epithelium within the macula, and by other abnormalities of the retinal pigment epithelium, including retinal cell death.

Although the exact etiology of ARMD is not known, several risk factors seem to be important for the manifestation of this disease. For example, ARMD may be caused by chronic exposure of the retina to light. The presence or absence of certain nutrients in the diet, such as the antioxidant vitamins E and C, also may affect one's predisposition for ARMD. Other conditions, such as hypertension and smoking, are also considered to be important risk factors for the development of this disease.

Recent histopathologic studies show that leukocytes and chronic inflammation may play a role in the pathogenesis of atrophic NE-ARMD (Penfold PL et al., Senile macular degeneration: The involvement of giant cells in the atrophy of the retinal pigment epithelium. Invest. Ophthalmol. Vis. Sci. 1986; 27: 364–371) and E-ARMD (Penfold PL et al., Age-related macular degeneration: Ultrastructural studies of the relationship of leucocytes to angiogenesis. Graefe's Arch. Ophthalmol. 1987; 2256: 70–76).

Several therapeutic methods have been tried. For example, vitamins and dietary supplements have been used for the purpose of delaying the onset of disease. Thalidomide is being investigated to determine if it will slow down or arrest new vessel formation. Laser or radiation has been used to destroy new vessels. However, none of these methods has led to successful results and no definitive treatment for ARMD has been developed to date.

2. SUMMARY OF THE INVENTION

The present invention is directed to the treatment of both E-ARMD and NE-ARMD by the long-term administration of antibiotics in therapeutically effective dosages which are safe for such prolonged usages. In one embodiment, a broad-spectrum, bacteriostatic antibiotic, such as tetracycline (250–1000 mg per day) is orally administered for six (6) weeks to fourteen (14) months.

Tetracyclines are broad spectrum bacteriostatic antibiotics known to have "collagenase inhibition properties, antioxidant activity, inhibition of protein synthesis in rapidly dividing cells, perturbation of leukocyte functions, interference with lymphocyte proliferation and anti-inflammatory effects" (Tilley BC et al., Minocycline in rheumatoid arthritis. A forty-eight (48) week double blind placebo controlled trial. MIRA trial Group. *Annals of Internal Medicine.* 1995; 122(2): 81–89). Forty-eight (48) week therapy with TBA has been shown to moderate the signs and symptoms of inflammatory diseases such as rheumatoid arthritis (Tilley BC et al., Minocycline in rheumatoid arthritis. A forty-eight (48) week double blind placebo controlled trial. MIRA trial Group. *Annals of Internal Medicine.* 1995; 122(2): 81–89). Its limited toxicity has enabled it to be used chronically as therapy for diverse diseases including acne rosacea (Brown SI et al., Diagnosis and treatment of ocular rosacea. *Ophthalmology.* 1978; 85: 779–786) which is commonly seen in the elderly. Animal studies reveal that intravenous tetracycline achieves high concentrations in the uvea and retina (Salamon SM, Tetracyclines in ophthalmology. *Sury. Ophthalmol.* 1985; 29: 265–275).

In addition to tetracycline, other antibiotics may be used, including tetracycline derivatives, such as minocycline, doxycycline, and oxycycline, but most preferably minocycline (100–200 mg per day); rifamycin and its derivatives, such as rifabutin (150–300 mg per day) and rifampin (150–300 mg per day), but most preferably rifabutin;

macrolides, such as azithromycin, erythromycin, and clarithromycin, but most preferably azithromycin (250–500 mg per day) and erythromycin (400–1200 mg per day as ethyl succinate); and metronidazole (375 mg per day). Furthermore, antibiotics can be administered orally or parenterally, including intravenously, intramuscularly, or subcutaneously, as the case may be for the particular antibiotic and the modes of administration of these clinically recognized antibiotics are already set in the literature.

The invention is based, in part, on the discovery that the administration of certain antibiotics, especially tetracycline-based antibiotics (TBA), to individuals with ARMD for unrelated non-ocular diseases for a period of up to fourteen (14) months, led to measurable improvements in visual acuity and in peripheral fields when there was such loss.

3. BRIEF DESCRIPTION OF THE DRAWINGS

FIG. 1 is a graph showing the study results wherein initial (before the treatment) vs. final (12 months after the commencement of treatment) acuity of studied eyes (n=20) is plotted. Numbers on or above diagonal dotted line represent number of eyes which improved two or more Snellen lines.

4. DESCRIPTION OF PREFERRED EMBODIMENTS

In a retrospective study, ten (10) patients with grade 3 or grade 4 (Bressler NM et al., The grading and prevalence of macular degeneration in Chesapeake By waterman. *Arch. Ophthalmol.* 1989; 107: 847–852) NE-ARMD and a varied medical history including chronic rheumatoid arthritis, acne rosacea, or chronic dermatitis without keratitis, were treated with either tetracycline (250 mg, b.i.d.) or minocycline (100 mg, q.d.) for up to fourteen (14) months for treatment of the non-ocular diseases. Visual acuity was followed for up to fourteen (14) months or average twelve (12) months. All individuals had received initial ophthalmologic examinations, including fluorescein angiography which revealed ARMD only. No individual exhibited corneal or intra-ocular inflammatory diseases. The study included 6 females and 4 males and the average age was 79 years old.

Forty percent of the eyes demonstrated improvements in visual acuity, being equal to or greater than two Snellen lines, when measured twelve (12) months after the commencement of treatment. This percentage was significantly greater ($p<0.05$) than the four percent of NE-ARMD patients who spontaneously exhibited equivalent improvements (Smiddy W. E. et al., Prognosis of patients with bilateral macular drusen. *Ophthalmology* 1984; 91: 271–276). Improvements were gradual, occurring only after three (3) to six (6) months of therapy. There were no detectable funduscopic changes. The vision of two patients deteriorated after stopping therapy for two (2) to three (3) months and subsequently improved again upon resuming therapy. Two eyes demonstrated visual field improvements.

The results, as shown in FIG. 1., suggest that the improvements in vision were produced by the TBA affecting the ARMD. The absence of corneal disease and the protracted course of gradual improvement make it unlikely that we were treating ocular acne rosacea. All acne rosacea patients treated by Brown and Shahinian showed an improvement within three (3) weeks of starting TBA therapy (Brown SI et al., Diagnosis and treatment of ocular rosacea. *Ophthalmology* 1978; 85: 779–786). We are not aware of any retinal manifestations of acne rosacea or that chronic rheumatoid arthritis and acne rosacea are risk factors for ARMD. The literature reveals no reports similar to this study.

What is claimed is:

1. A method for the treatment of age-related macular degeneration, comprising systemically administering a therapeutically effective but safe amount of tetracycline for a therapeutically effective period to a patient in need thereof.

2. The method according to claim 1, wherein the tetracycline is orally administered in a dosage between 250 and 1000 mg per day.

3. The method according to claim 1, wherein the tetracycline is administered for at least six weeks.

4. A method for the treatment of age-related macular degeneration, comprising systemically administering a therapeutically effective but safe amount of minocycline for a therapeutically effective period to a patient in need thereof.

5. The method according to claim 4, wherein the minocycline is orally administered in a dosage between 100 and 200 mg per day.

6. The method according to claim 4, wherein the minocycline is administered for at least six weeks.

* * * * *

UNITED STATES PATENT AND TRADEMARK OFFICE
CERTIFICATE OF CORRECTION

PATENT NO.    : 6,015,803

DATED         : January 18, 2000

INVENTOR(S)   : Emil WIROSTKO

It is certified that error appears in the above-identified patent and that said Letters Patent is hereby corrected as shown below:

On the title page, item:
   [22] Filing date, change "May 5, 1998" to --May 4, 1998--.

Signed and Sealed this

Tenth Day of October, 2000

Attest:

Q. TODD DICKINSON

*Attesting Officer*          *Director of Patents and Trademarks*